United States Patent [19]
Augustine et al.

[11] Patent Number: 5,300,101
[45] Date of Patent: Apr. 5, 1994

[54] METHOD AND APPARATUS FOR TREATMENT OF PEDIATRIC HYPOTHERMIA

[75] Inventors: Scott D. Augustine, Bloomington; Randall C. Arnold, Minnetonka; Thomas P. Anderson, Savage, all of Minn.

[73] Assignee: Augustine Medical, Inc., Eden Prairie, Minn.

[21] Appl. No.: 729,051

[22] Filed: Jul. 12, 1991

Related U.S. Application Data

[63] Continuation-in-part of Ser. No. 227,189, Aug. 2, 1988, abandoned, which is a continuation-in-part of Ser. No. 104,682, Oct. 5, 1987, abandoned.

[51] Int. Cl.$^5$ .............................................. A61F 7/00
[52] U.S. Cl. ...................................... 607/107; 5/482
[58] Field of Search ............... 128/349, 480, 402, 376, 128/374; 165/46; 62/259.3; 5/423, 482, 485; 219/211, 212

[56] References Cited

U.S. PATENT DOCUMENTS

| | | | |
|---|---|---|---|
| 2,110,022 | 3/1938 | Kliesrath | 5/423 |
| 2,512,559 | 6/1950 | Williams | 5/423 |
| 3,757,366 | 9/1973 | Sacher | 128/400 |
| 4,139,004 | 2/1979 | Gonzalez | 128/402 |
| 5,165,400 | 11/1992 | Berke | 128/400 |

FOREIGN PATENT DOCUMENTS

| | | | |
|---|---|---|---|
| 113420 | 7/1984 | European Pat. Off. | |
| 883091910 | 3/1988 | European Pat. Off. | A61F 7/00 |

OTHER PUBLICATIONS

Warmair Hyperthermia System, Cincinnati Sub Zero Products, Inc., two-page advertisement.

Primary Examiner—Mark S. Graham
Attorney, Agent, or Firm—Baker, Maxham, Jester & Meador

[57] ABSTRACT

An inflatable chamber which is formable into a generally U-shaped structure includes an air inlet for receiving a thermally-controlled inflating medium and a plurality of holes in a side portion. When the medium is received in the chamber, it is expelled through the holes and bathes a patient to effect hypothermia treatment. In addition, the apparatus may include selectively positionable non-inflatable coverings for selectively warming pediatric patient body portions while leaving other portions exposed to untreated ambient air.

22 Claims, 3 Drawing Sheets

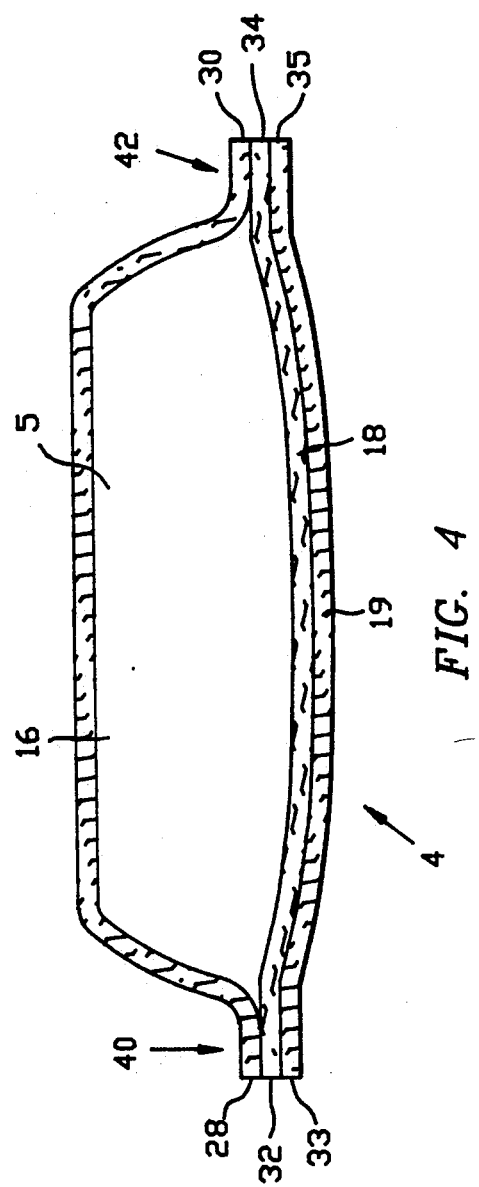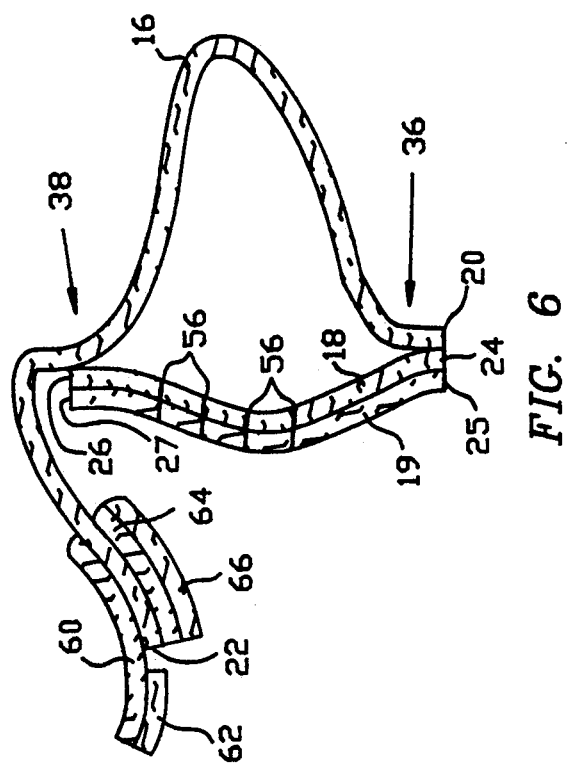

METHOD AND APPARATUS FOR TREATMENT OF PEDIATRIC HYPOTHERMIA

CROSS-REFERENCE TO RELATED APPLICATION

This is a continuation-in-part of U.S. patent application Ser. No. 07/227,189, filed Aug. 2, 1988, abandoned which is a continuation-in-part of application Ser. No. 07,104,682, filed Oct. 5, 1987, abandoned.

This application contains material related to the subject of U.S. patent application Ser. No. 07/638,748, pending, assigned commonly herewith.

BACKGROUND OF THE INVENTION

This invention relates to inflatable structures for treatment of hypothermia, and is used in a medical setting to deliver a bath of a thermally-controlled medium to a patient. In particular, the thermally-controlled medium is used to inflate the structure and is expelled therefrom onto a patient. Still more particularly, the invention relates to inflatable structures for the treatment of hypothermia in infants and small children.

The relevant art is perhaps best expressed in U.S. Pat. No. 4,572,188 entitled "AIRFLOW COVER FOR CONTROLLING BODY TEMPERATURE," and commonly assigned with this application. In the prior patent, a self-erecting, inflatable airflow cover is inflated by the introduction into the cover of a thermally-controlled inflating medium, such as warmed air. When inflated, the cover self-erects about a patient, thereby creating an ambient environment about the patient, the thermal characteristics of which are determined by the temperature of the inflating medium. Holes on the underside of the prior art airflow cover exhaust the thermally-controlled, inflating medium from inside the cover to the interior of the erected structure. The airflow cover is intended for the treatment of hypothermia, as might occur operatively or postoperatively.

An alternative embodiment airflow device in the '188 patent includes an inflatable, annular tube which fits to a patient's head. Air holes are provided in the tube, as is an entry port. A sheet of material attached to one side of the annular tube retains a warmed inflating medium within a circular space that contains the top of a patient's head. An exit port is cut in the sheet to exhaust the inflating medium from within the structure.

Evaluation of the airflow cover described in the '188 patent by skilled practitioners has resulted in general approbation: the opinion is that the airflow cover efficiently and effectively accomplishes its purpose of giving a thermally-controlled bath. However, since the airflow cover extends unbrokenly from the feet to the neck of a patient, it cannot be used in the operating room during surgery. In order to accommodate the essential structure of the airflow cover to use during surgery on clinical treatment, we have developed airflow covers suitable for thermal treatment of portions of the body during surgery. In particular, inflatable thermal blankets for covering particular body portions while surgery is conducted on non-covered portions are described and illustrated in the cross-referenced U.S. patent application Ser. No. 07/638,748.

The positive result obtained from use of the airflow cover and body portion thermal blankets notwithstanding, thermal maintenance of pediatrics patients during and after surgery presents a new challenge. Particularly, such a patient must receive a supply of heated air which is adequate for thermal treatment, which is appropriate to the size of the patient, and which provides access to a care site. In particular, we have realized that a need exists for an inflatable apparatus for thermally treating infants and small children both operatively and postoperatively.

SUMMARY OF THE INVENTION

In meeting the challenge of thermally treating pediatrics patients, we have improved the clinical usefulness of our present thermal blankets by observing that infants and small children can be successfully thermally controlled by an inflatable structure which directs warmed air into a thermal bathing space to warm selected portions of the patient while leaving other patient body portions, such as a surgical care site, exposed for access.

In particular, an inflatable apparatus for treatment of pediatric hypothermia includes an elongate inflatable chamber formable into an inflatable enclosure that surrounds a patient and defines a thermal care space. A plurality of exhaust ports open through a side portion of the inflatable chamber from which they exhaust the inflating medium from the chamber toward a patient placed in the thermal care space. Positionable non-inflatable covering sheets are employed to direct the inflating medium to selected patient body portions while leaving other portions exposed to untreated ambient air. These extend across the patient and the enclosure to confine the inflating medium to the thermal care space. The sheets may be positioned on the enclosure and patient such that a surgical care site on a portion of the patient's body is trunk is entirely covered.

With these improvements, the apparatus, when inflated and positioned about a patient, delivers the thermally-controlled inflating medium to the thermal care space, thereby thermally bathing the patient. The inflatable chamber arrangement with positionable coverings facilitates thermal care of infants or small children where selective application of thermal treatment is required.

Therefore the invention accomplishes the important objective of providing a self-erecting, inflatable thermal apparatus that provides effective treatment of hypothermia to a pediatric patient.

A still further objective is the provision of an apparatus adapted for the delivery of a thermally-controlled medium to selected portions of a patient while leaving other patient body portions, such as a care site, exposed for treatment.

The uncomplicated construction of the thermal care apparatus makes its production straightforward and economical. Also, the simple structure is more readily adaptable to the small size of a pediatric patient than the airflow cover and body portion thermal blankets of the cross-referenced patent applications.

These and other important objectives and advantages will become evident when the detailed description of the invention is read with reference to the below-summarized drawings, in which:

FIG. 4 is a sectional view taken along line B—B in FIG. 2.

FIG. 6 is a sectional view taken along line C—C in FIG. 1, showing the inflatable body in an operational orientation with associated thermal control components.

DETAILED DESCRIPTION OF THE PREFERRED EMBODIMENTS

Figure 1:
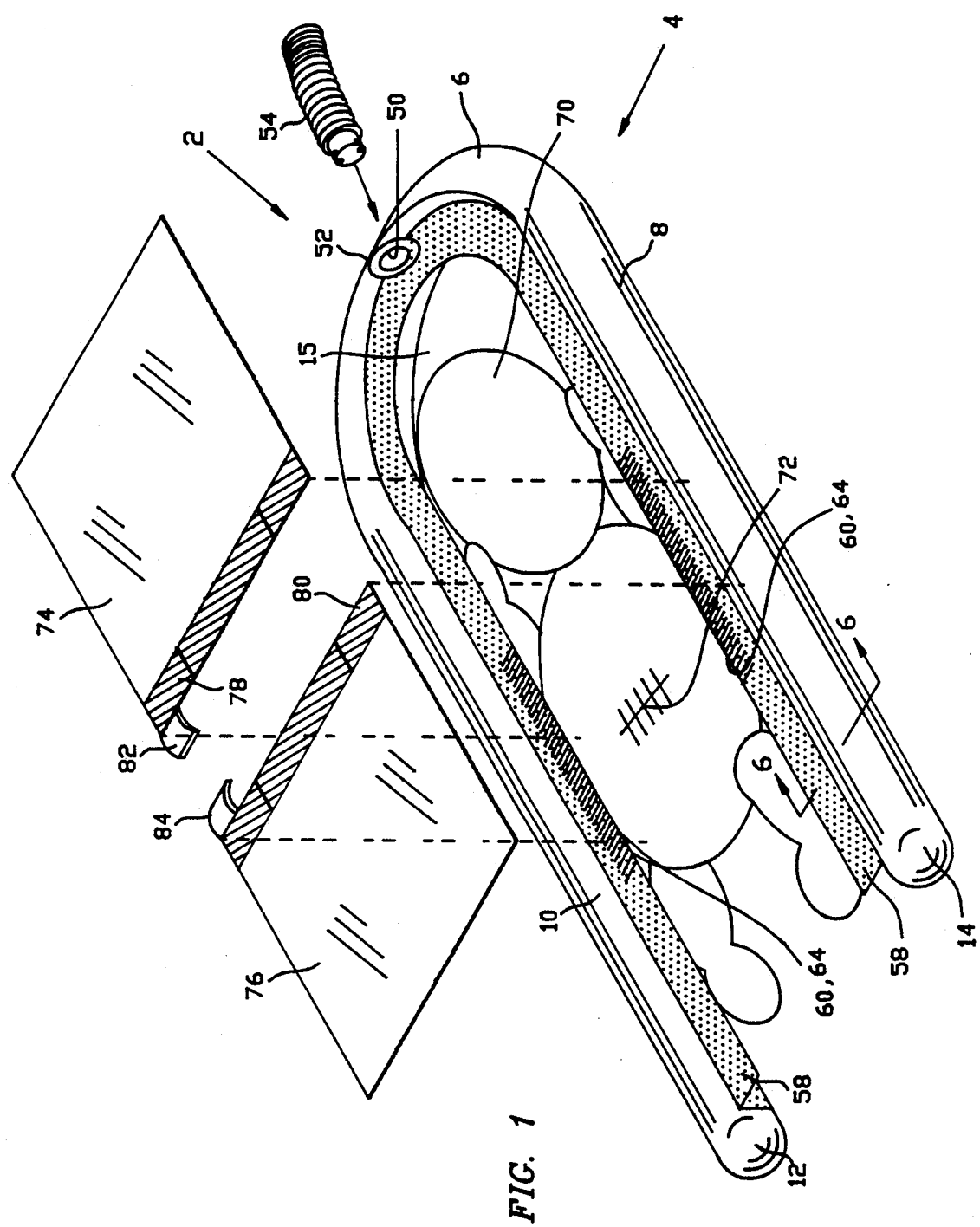
FIG. 1 is a projected diagrammatic illustration of a pediatric thermal warming apparatus constructed in accordance with the present invention, as shown in one operational configuration with an elongated inflatable chamber arranged around a patient to define a thermal care space.

Referring now to the Figures, a thermal treatment apparatus 2 for use with pediatric patients includes an elongated inflatable body 4, defining an interior inflatable chamber 5. The inflatable body 4 is generally tubular in shape and made from an air impermeable material such as plastic. The inflatable body 4 may be arranged around a patient in a variety of configurations to form a thermal care space. For example, as shown in FIG. 1, the inflatable body 4 could be formed in a generally U-shaped configuration. With the inflatable body oriented as shown in FIG. 1, there is provided a chamber with a central base 6 extending to a pair of sides 8 and 10 which terminate at respective terminal ends 12 and 14. As so configured, a thermal care space 15 extending from the base 6 to the terminal ends 12 and 14, and between the sides 8 and 10, is provided. Preferably, the inflatable body 4 is not less than about four inches in diameter in order to properly cover a pediatric patient placed in the interior thermal bathing space 15. Other diameters could also be used depending on anticipated patient size. Moreover, although FIG. 1 illustrates a configuration wherein the patient's head is positioned at the base 6, the patient could be positioned with the head at the terminal ends 8 and 10, where, for example, care is to be given to the patient's head or neck areas. It will be further appreciated that the inflatable body 4 could be arranged to form other shapes as necessary to define a preferred thermal bathing area, the U-shape of FIG. 1 being shown merely for illustration purposes.

CONSTRUCTION

Figure 2:
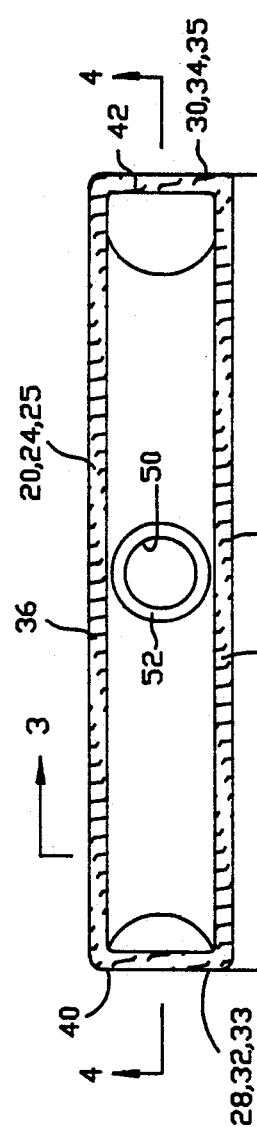
FIG. 2 is a side elevation view showing the inflatable body of FIG. 1 fully extended to illustrate the construction thereof.
Figure 3:
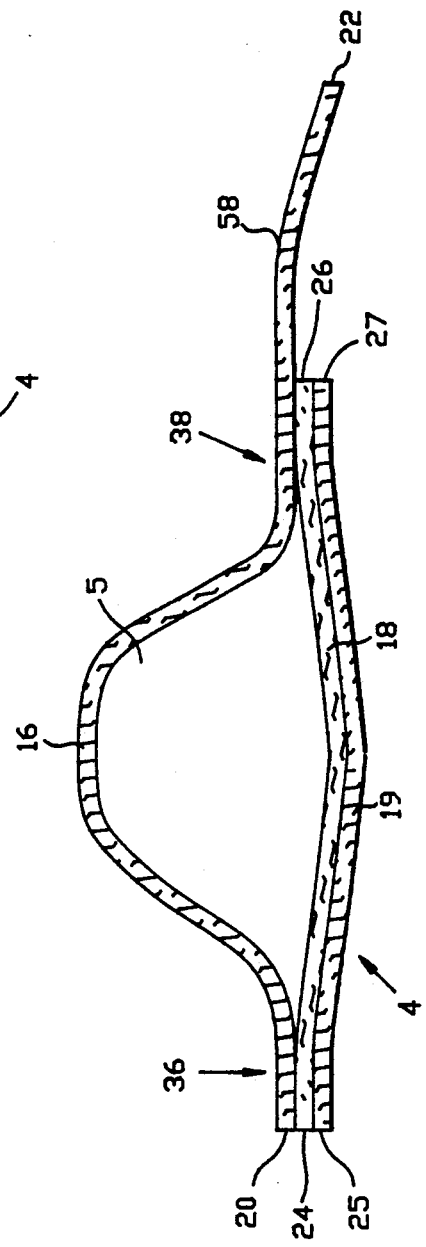
FIG. 3 is a sectional view taken along line A—A in FIG. 2.

A preferred construction for our thermal treatment apparatus is illustrated in FIGS. 2, 3 and 4, wherein the inflatable body 4 is shown in elongated form and not arranged about a patient. The inflatable body 4 is fabricated by bonding together a pair of generally rectangular sheets of air impermeable material. The material sheets are bonded along a continuous air impermeable seam to provide the inflatable chamber 5. A first material sheet 16, representing a cover sheet, is formed in the preferred construction from a single layer of flexible plastic sheet material. A second material sheet 17, representing a base sheet, is made from an upper layer 18 of flexible plastic sheet material, and further includes a lower layer 19 made from absorbant tissue paper or the like, which is laminated to the upper plastic layer 18. As shown in FIGS. 2 and 3, the cover and base sheets 16 and 17 are dimensionally similar in the longitudinal direction. In the lateral direction, however, the cover sheet 16 is substantially wider than the base sheet. This difference in lateral dimension facilitates the economic construction of the inflatable body, as will now be described.

To form the inflatable body 4, the cover sheet 16 is bonded to the upper layer 18 of the base sheet by a heat bonding process to form a continuous peripheral seam. The peripheral seam is formed with reference to the respective longitudinal and lateral end edges of the cover and base sheets. As will be noted from the Figures, the cover sheet 16 includes two longitudinal edges 20 and 22. The base sheet includes two longitudinal edges 24 and 26 of the upper layer 18, and two longitudinal edges 25 and 27 of the lower layer 19. As will be further noted from the Figures, the cover sheet includes two lateral end edges 28 and 30. The base sheet includes two lateral end edges 32 and 34 of the upper layer 18, and two lateral end edges 33 and 35 of the lower layer 19. A first longitudinal seam 36 is formed by heat bonding the cover and base sheets together along the respective longitudinal edges 20 and 24. Likewise, a pair of lateral end seams 40 and 42 are formed by heat bonding the cover and base sheets together along the lateral end edges 28, 32 and 30, 34, respectively. A final longitudinal seam 38 is formed by heat bonding the longitudinal edge 26 of the upper base sheet layer 18 to an intermediate longitudinal portion of the cover sheet 16. As shown in FIG. 3, the cover sheet 16 is thus formed to include a mounting strip extension 58 which, as described in more detail below, is useful for anchoring the inflatable body 4 to a patient. In combination, the seams 36, 38, 40 and 42 form a continuous air impermeable seam that seals the interior of the inflatable body 4 for retaining an inflating medium such as air in the inflatable chamber 5. The seam will therefore be of sufficient width, ¼ inches for example, to provide an effective seal against the inflating medium.

A plurality of base sheet apertures 43 are opened through the base sheet 17 prior to bonding the cover and base sheets as described above. These apertures extend through the upper and lower layers 18 and 19 of the base sheet 17.

Figure 5:
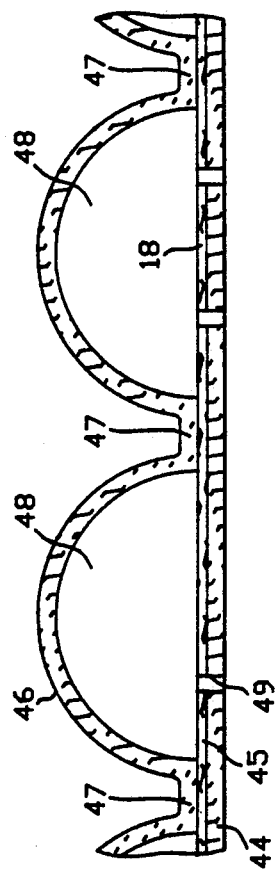
FIG. 5 is a further enlarged sectional view showing a potential method of manufacture of a pediatric thermal warming apparatus constructed in accordance with the present invention.

As thus far described, the tubular construction of the apparatus of the invention is substantially identical in most important respects with the construction of the inflatable tubes which form the thermal blanket in U.S. patent application Ser. No. 07/227,189, referenced above. FIG. 5 reproduces the tubular construction of the thermal blanket in that patent application.

Referring now to FIG. 5, the thermal blanket is assembled from a base sheet consisting of an underside layer 44 formed from flexible material capable of bonding to an upper layer 45 of heat-sealable plastic. For the layers 44 and 45, a stratum of absorbent tissue paper prelaminated with a layer of heat-sealable plastic is used. Material of such construction is commercially available in production rolls and is used to make painters' drop cloths. The upper side of the thermal blanket consists of the sheet of plastic 46 bonded to the plastic layer 45 by a heat-sealing process to form longitudinal seams 47, and inflatable chambers 48. A plurality of apertures 49 extend through the layers 44 and 45 of the base sheet.

As indicated, the inflatable body 4 may be formed into a generally U-shaped configuration having a central base 6, a pair of sides 8 and 10, and a pair of terminal ends 12 and 14. To facilitate that formation, and to avoid kinks or creases that might restrict the flow of an inflating medium, the inflatable body 4 is oriented with the edge seams 36, 38, 40 and 42 oriented in a generally vertical plane, as shown in FIGS. 1 and 6. The inflatable body 4 is provided at the base 6 with a circular inlet aperture 50 and an attached female coupling 52 conveniently formed from reinforced paper or cardboard material, and sized and adapted to receive the end of an air inlet duct 54. The air inlet duct 54 may be attached to a thermal control apparatus 18, described in more detail below, including a heater/blower operable to provide an input flow of heated air through the inlet manifold 52 at a rate sufficient to fully inflate the body 4 without causing it to burst. Although FIG. 1 illustrates the placement of an inlet at the base 6, it will be appreciated that other inlet positioning arrangements may also be possible provided a relatively uniform temperature profile along the inflatable body is maintained. Thus, for example, a pair of inlets could be provided at the terminal ends 12 and 14.

As further shown in FIGS. 1, 2 and 6, the plurality of exhaust ports 43 formed in the base sheet permit warmed air introduced through the inlet 50 to flow out of the inflatable chamber 5 to the thermal care space 15 formed by the arrangement of the body 4. As further shown in FIG. 6, and as previously described, the cover sheet 16 includes a mounting strip extension 58, extending between the longitudinal edge 22 of the cover sheet 16 and the longitudinal edge 26 of the base sheet layer 18. The mounting strip 58 is oriented inwardly from the body 4, toward the thermal bathing space 15. It has attached thereto, at the longitudinal edge 22, an adhesive strip. In one preferred construction, the adhesive strip includes a tape element 60 which is adhered to the upper side of the mounting strip 58 so that an exposed portion of the tape element extends beyond the longitudinal edge 22. The adhesive tape element 60 has a protective peel-off backing 62 mounted over the exposed adhesive portion thereof. In another preferred construction, the adhesive strip includes a double sided adhesive tape element 64, one side of which is adhered to the underside of the mounting strip 58. The other adhesive side is covered by a protective peel-off backing 66.

METHOD OF OPERATION

Referring now to FIG. 1, the space 15 formed by the arrangement of the inflatable body 4 provides a thermal warming zone within which a small child or infant 70 may be placed. As indicated, the patient could be positioned as shown in FIG. 1, or in a reversed position with the patient's head placed at the terminal ends 12 and 14. The child could be so positioned for thermal care during or after a medical treatment procedure. In FIG. 1, the child is positioned to undergo a surgical procedure conducted at a care site 72. The inflatable body 4 is positionally maintained adjacent the patient using the adhesive strips 60 or 64. The adhesive strips are removably adhered to the patient's torso, arms and/or legs at locations generally laterally adjacent the patient care site.

As shown in FIG. 1, the exhaust ports 43 direct a thermal inflating medium used to fill the inflatable chamber 5 as a thermal bath towards the patient 70 placed within the thermal bathing space 15. In order to retain a thermal inflating medium around the patient, but away from the care site, a pair of non-inflatable, plastic covers 74 and 76 may be placed over the patient. The covers are affixed to the patient by means of adhesive strips 78 and 80 which, before use, are protected by peel-off backings 82 and 84, respectively. It will be appreciated that the covers 74 and 76 may be placed independently of one another and of the chamber 5 so as not to cover the surgical site 72 on the patient 70. Thus, if the surgical site 72 is for an incision on the patient's abdomen, the cover 74 would be placed above the incision site to extend over the patient's upper torso, head and arms. The cover 76 would be situated slightly below the incision 72 to extend over the patient's lower torso, legs and feet. As indicated, to assist in positioning the covers 74 and 76, each is provided with a strip of adhesive material such as tape 78 and 80, respectively, which may be removably adhered to the patient's skin. As shown in FIG. 1, the covers 74 and 76 operate in conjunction with the mounting strip 58 to define a care site from which the thermal bath immersing the patient is excluded. The lateral extent of the care site is defined by adherence of the adhesive strips 60 or 64 to the patient. The longitudinal extent of the care site is defined by adherence of the adhesive strips 78 and 80 to the patient.

The above-described apparatus provides a pediatric thermal control system for providing selected areas of a small patient with a thermal bath, while leaving other areas, such as a surgical site exposed to untreated ambient air to facilitate proper treatment. This system may be operated in accordance with a method wherein a small child or infant is supported by a bed or similar support surface and provided with a thermal treatment by first placing the uninflated thermal warming apparatus 2 around the patient, with the air inlet 50 above the patient's head and the ends 12 and 14 positioned adjacent the patient's feet. Alternatively, if care is to be provided to the patient's head, neck or adjacent areas, the air inlet 50 could be placed at the patient's feet and the ends 12 and 14 could be positioned at the patient's head. The thermal control apparatus 2 is adhesively attached to the patient at locations laterally adjacent a care site. The apparatus inlet 50 is connected to the air duct 54, which is itself operatively attached to a heater/blower assembly 90 that provides a stream of heated air through the air duct 54 to inflate the thermal control apparatus 2. With the apparatus inflated and the apertures 43 directing a thermally-controlled bath towards the patient, the patient is selectively covered using one or more of the covers 74 and 76, which are adhesively mounted to the patient's skin at locations longitudinally adjacent the care site.

Many modifications and variations of our invention will be evident to those skilled in the art. For example, thermal coverings for additional selected patient areas could be implemented depending on the location of the care site and the need for thermally maintaining other areas. It is understood that such variations may deviate from specific teachings of this description without departing from the essence of the invention, which is expressed in the following claims.

We claim:

1. A pediatric thermal treatment apparatus for covering and bathing a small child or infant in a thermally-controlled inflating medium, comprising:

a single inflatable chamber arrangeable in a generally U-shaped configuration defined by a base portion and a pair of side portions extending to a pair of terminal end portions, said configuration defining a thermal care zone for receiving a patent;

said base portion having a substantially continuous curvature and said U-shaped configuration including a substantially continuously curved transition between said base portion and each of said side portions;

an air inlet disposed in said inflatable chamber for receiving a thermally-controlled inflating medium into said inflatable chamber;

a plurality of exhaust ports formed in said inflatable chamber for exhausting an inflating medium from said inflatable chamber toward said thermal care zone; and means on each of said side portions for positionally retaining said apparatus laterally adjacent a patent by acting between said each of said side portions and said patient.

2. The thermal treatment apparatus of claim 1 wherein said means for positionally retaining include means for adhesively affixing said apparatus to a patient.

3. The thermal treatment apparatus of claim 1 further including at least one cover sheet extending between said side portions for retaining a thermally-controlled inflating medium exhausted from said exhaust ports in said thermal care zone.

4. The thermal treatment apparatus of claim 3 wherein said cover sheet includes means for adhesively affixing said sheet to a patient.

5. The thermal treatment apparatus of claim 1, said means for positionally retaining including an attachment strip mounted to said side portions for adhesively mounting said apparatus to a patient.

6. The thermal treatment apparatus of claim 5 wherein said attachment strip includes an adhesive strip mounted to the underside thereof for removably adhering said apparatus to a patient.

7. The thermal treatment apparatus of claim 1 wherein said inflatable chamber is defined by a cover sheet, a base sheet and a continuous seam extending around the periphery of and joining said sheets to form an air impermeable seal, said inflatable chamber inflating in response to receipt of a thermally-controlled inflating medium, said continuous seam being substantially vertically oriented in response to said inflation.

8. The thermal treatment apparatus of claim 7 wherein said base sheet is formed from a material including a layer of plastic and a layer of flexible material to which the layer of plastic is bonded.

9. The thermal treatment apparatus of claim 3 including two cover sheets positionable to cover portions of a patient's body while exposing other body portions to untreated ambient air.

10. A thermal control apparatus for selectively bathing body portions of patient in a thermally-controlled inflating medium comprising:

inflatable chambers positionable adjacent a patient to be thermally bathed to form a thermal bathing zone for said patient;

said inflatable chambers including side portions for disposition laterally of, and adjacent to, said patient;

an air inlet in fluid communication with said chambers for receiving a thermally-controlled inflating medium into said chambers;

a plurality of air exhaust ports formed in said side portions of said chambers for exhausting inflating medium from said chambers to said thermal bathing zone;

an adjustable cover removably mountable on said chambers, said cover being adjustable to selectively bathe body portions of a patient in said thermal bathing area while exposing other body portions to untreated ambient air; and means on said side portions of said chambers for removably attaching each of said side portions to said patient.

11. The thermal control apparatus of claim 10 wherein said chambers include a generally transverse central base chamber defining a base portion of said thermal bathing area, and a pair of generally longitudinal side chambers extending from said base chamber to define said side portions.

12. The thermal control apparatus of claim 11 wherein said exhaust ports are arranged in an array extending in said base and side chamber portions.

13. The thermal control apparatus of claim 11 wherein said means on said side chambers include an attachment for removably mounting said side chambers to said patient.

14. The thermal control apparatus of claim 13 wherein said attachment includes an adhesive strip mounted to said side chambers for attaching said side chambers to said patient.

15. The thermal control apparatus of claim 10, wherein said adjustable cover includes a pair of non-overlapping sheet elements removably mountable to said patient and extending over selected portions of said patient to retain said exhaust inflating medium over said selected patient portions while exposing non-selected patient portions to untreated ambient air.

16. The thermal control apparatus of claim 15 wherein said sheet elements are adhesively mountable to said patient.

17. The thermal control apparatus of claim 10, wherein said chambers form a single tubular structure, said single tubular structure including:

a first sheet;

a second sheet bonded to said first sheet by a continuous peripheral seam;

a plurality of apertures opening through said first sheet into said single tubular structure;

said tubular structure being inflatable in response to receipt of a thermally-controlled inflating medium; and said peripheral seam being substantially vertically oriented in response to said inflation.

18. The thermal control apparatus of claim 17, wherein said single tubular structure includes a flat, non-inflatable portion which extends beyond said peripheral seam, away from said apertures, said means on said side portions being fixed to said single tubular structure on said non-inflatable portion.

19. The thermal control apparatus of claim 18, wherein said means on said side portions includes an adhesive strip.

20. A method for bathing selected portions of a patient in a thermally-controlled inflating medium, comprising the steps of:

supporting a patient to be treated on a support surface;

arranging said patient an inflatable around chamber apparatus to form a thermal bathing zone containing said patient, said inflatable chamber apparatus including at least one inflatable chamber in fluid communication with an air inlet for receiving a thermally-controlled inflating medium into said chamber, said chamber further including a plurality of air exhaust ports formed in a side portion of said chamber for exhausting an inflating medium from said chamber to said thermal bathing zone;

affixing said inflatable chamber to selected portions of said patient;

connecting said air inlet to a source of a thermally-controlled inflating medium capable of inflating said chamber;

removably affixing to said patient a covering extending over selected portions of said thermal bathing zone to direct a thermally-controlled inflating medium exhausted from said chamber to selected body portions of said patient while leaving other patient body portions exposed to untreated ambient air; and operating said thermally-controlled medium to direct said thermally-controlled inflating medium to said selected patient body portions for a time sufficient to thermally treat said patient.

21. The method of claim 20 wherein said inflatable chamber is adhesively bonded to said patient.

22. The method of claim 21 wherein said covering includes a pair of sheets having adhesive strips thereon and said step of selected affixation of said covering includes the step of adhering one of said sheets to a first portion of said patient and adhering the second of said sheets to a second portion of said patient.

* * * * *

UNITED STATES PATENT AND TRADEMARK OFFICE
CERTIFICATE OF CORRECTION

PATENT NO.   : 5,300,101
DATED        : April 5, 1994
INVENTOR(S)  : Scott D. Augustine et al.

It is certified that error appears in the above-indentified patent and that said Letters Patent is hereby corrected as shown below:

```
Column 6, line 65, change "patent" to --patient--.
Column 7, line 11, change "patent" to --patient--.
Column 8, lines 60-61, insert after "arranging" the word --around--
    and after "inflatable" delete the word --around--.
```

Signed and Sealed this

Fourteenth Day of February, 1995

Attest:

BRUCE LEHMAN

Attesting Officer          Commissioner of Patents and Trademarks